(12) United States Patent
Olivero

(10) Patent No.: US 11,950,886 B2
(45) Date of Patent: Apr. 9, 2024

(54) APPARATUS AND METHOD FOR PROVIDING REMOTE HEALTH CARE RECOMMENDATIONS USING A PASSIVE HEALTH CARE MONITORING DEVICE

(71) Applicant: Anthony Olivero, Ada, MI (US)

(72) Inventor: Anthony Olivero, Ada, MI (US)

( * ) Notice: Subject to any disclaimer, the term of this patent is extended or adjusted under 35 U.S.C. 154(b) by 309 days.

(21) Appl. No.: 17/337,949

(22) Filed: Jun. 3, 2021

(65) Prior Publication Data

US 2021/0290083 A1    Sep. 23, 2021

Related U.S. Application Data

(63) Continuation-in-part of application No. 16/668,759, filed on Oct. 30, 2019, which is a continuation of application No. 16/003,377, filed on Jun. 8, 2018, now Pat. No. 10,492,696.

(60) Provisional application No. 62/517,250, filed on Jun. 9, 2017.

(51) Int. Cl.
| | | |
|---|---|---|
| *A61B 5/0205* | (2006.01) | |
| *A61B 5/00* | (2006.01) | |
| *A61B 5/01* | (2006.01) | |
| *A61B 5/024* | (2006.01) | |
| *A61B 5/08* | (2006.01) | |
| *A61B 5/11* | (2006.01) | |
| *A61B 5/145* | (2006.01) | |

(52) U.S. Cl.
CPC ........ *A61B 5/02055* (2013.01); *A61B 5/0022* (2013.01); *A61B 5/6831* (2013.01); *A61B 5/01* (2013.01); *A61B 5/02438* (2013.01); *A61B 5/0816* (2013.01); *A61B 5/1112* (2013.01); *A61B 5/14542* (2013.01); *A61B 2562/066* (2013.01)

(58) Field of Classification Search
CPC . A61B 5/02055; A61B 5/0022; A61B 5/6831; A61B 5/01; A61B 5/02438; A61B 5/0816; A61B 5/1112; A61B 5/14542; A61B 2562/066; G16H 20/13; G16H 20/70; G16H 40/20; G16H 40/63; G16H 40/67; G16H 50/70
See application file for complete search history.

(56) References Cited

U.S. PATENT DOCUMENTS

| | | | |
|---|---|---|---|
| 6,450,955 | B1 | 9/2002 | Brown |
| 8,107,920 | B2 | 1/2012 | Ben Ayed |
| 8,503,972 | B2 | 8/2013 | Haler |
| 9,041,530 | B2 | 5/2015 | Sprigg et al. |
| 9,277,870 | B2 | 3/2016 | Spolin et al. |

(Continued)

*Primary Examiner* — Daryl C Pope
(74) *Attorney, Agent, or Firm* — Price Heneveld LLP

(57) ABSTRACT

A portable biometric healthcare interface includes a wearable member having a plurality of sensors incorporated therein. Each sensor of the plurality of sensors is adapted to monitor a corresponding biometric indicator. A communications hub is in communication with the plurality of sensors. The wearable member and the communications hub cooperatively include a set of biometric parameters. Each biometric parameter of the set of biometric parameters includes a corresponding preferred range. At least one of the sensors indicates that the corresponding biometric indicator is outside of the corresponding preferred range. The communications hub provides a status indicia corresponding to a proposed recommendation.

20 Claims, 11 Drawing Sheets

(56) References Cited

U.S. PATENT DOCUMENTS

| | | |
|---|---|---|
| 9,456,787 B2 | 10/2016 | Venkatraman et al. |
| 10,007,771 B2 | 6/2018 | Oguz |
| 10,456,065 B2 | 10/2019 | Imran |
| 10,492,696 B2 * | 12/2019 | Olivero ................ A61B 5/0022 |
| 2005/0084075 A1 | 4/2005 | Kotzin |
| 2007/0204691 A1 | 9/2007 | Bogner et al. |
| 2009/0125327 A1 | 5/2009 | Peeters |
| 2015/0161876 A1 * | 6/2015 | Castillo .............. G08B 21/0446 340/539.11 |
| 2015/0370999 A1 | 12/2015 | Carpenter |
| 2015/0382086 A1 | 12/2015 | Kim et al. |
| 2016/0055758 A1 | 2/2016 | Francis |
| 2016/0324419 A1 | 11/2016 | Chang et al. |
| 2016/0330573 A1 | 11/2016 | Masoud et al. |
| 2016/0335871 A1 | 11/2016 | Kim et al. |
| 2016/0342744 A1 | 11/2016 | Joao |
| 2016/0353996 A1 | 12/2016 | Fink |
| 2016/0367157 A1 * | 12/2016 | Blake ..................... A61B 5/053 |
| 2016/0367188 A1 | 12/2016 | Malik et al. |
| 2017/0185284 A1 | 6/2017 | Bhavaraju et al. |
| 2017/0185953 A1 | 6/2017 | Dalforno et al. |

* cited by examiner

is hereby incorporated herein by

APPARATUS AND METHOD FOR PROVIDING REMOTE HEALTH CARE RECOMMENDATIONS USING A PASSIVE HEALTH CARE MONITORING DEVICE

CROSS-REFERENCE TO RELATED APPLICATIONS

The present application is a continuation-in-part of U.S. patent application Ser. No. 16/668,759 filed Oct. 30, 2019, entitled PORTABLE BIOMETRIC MONITORING DEVICE AND METHOD FOR USE THEREOF, which is a continuation of U.S. patent application Ser. No. 16/003,377 filed Jun. 8, 2018, entitled PORTABLE BIOMETRIC MONITORING DEVICE AND METHOD FOR USE THEREOF, now U.S. Pat. No. 10,492,696, which claims priority to and the benefit under 35 U.S.C. § 119(e) of U.S. Provisional Patent Application No. 62/517,250 filed on Jun. 9, 2017, entitled PORTABLE BIOMETRIC MONITORING DEVICE AND METHOD FOR USE THEREOF, the entire disclosures of which are hereby incorporated herein by reference.

FIELD OF THE INVENTION

The present invention generally relates to a biometric monitoring device, and more specifically, a device including sensors for monitoring the various biometric indicators related to an individual's current status with respect to various health and/or wellness parameters.

BACKGROUND OF THE INVENTION

Certain illnesses, such as bronchiolitis, can afflict individuals of a younger age and those with diminished immune systems. Bronchiolitis and other respiratory ailments can often be recurring and can last for an extended period of time. Additionally, these respiratory ailments can be highly contagious, such that they may spread rapidly through various geographic locations at any one time. Additionally, children with chronic illnesses suffer longer and more severe symptoms than otherwise healthy children. Early detection of these ailments can facilitate closer healthcare monitoring and interventions which may decrease the duration and severity of symptoms. This may reduce the degree and/or rate of geographic spread and inform healthy or immunocompromised individuals about locations where various illnesses may be prevalent at a particular time.

SUMMARY OF THE INVENTION

According to one aspect of the present invention, a portable biometric healthcare interface includes a wearable member having a plurality of sensors incorporated therein. Each sensor of the plurality of sensors is adapted to monitor a corresponding biometric indicator. A communications hub is in communication with the plurality of sensors. The wearable member and the communications hub cooperatively include a set of biometric parameters. Each biometric parameter of the set of biometric parameters includes a corresponding preferred range. At least one of the sensors indicates that the corresponding biometric indicator is outside of the corresponding preferred range. The communications hub provides a status indicia corresponding to a proposed recommendation.

According to another aspect of the present invention, a method of providing remote healthcare based upon monitored biometric function of an individual includes placing a wearable member onto a portion of an individual's body. A plurality of sensors within the wearable member are positioned to monitor corresponding biometric indicators. The method also includes monitoring the corresponding biometric indicators. Each biometric indicator is compared with a corresponding biometric parameter. Each corresponding biometric parameter includes a corresponding preferred range. A status indicia is provided when at least one of the biometric indicators falls outside the preferred range of the corresponding biometric indicators. A proposed recommendation is provided regarding actions to be taken with respect to the individual's body.

According to another aspect of the present invention, a method of monitoring a biometric function of an individual includes placing a wearable member onto a portion of an individual's body. A plurality of sensors within the wearable member are positioned to monitor corresponding biometric indicators. The plurality of sensors are placed in communication with a communications hub. The communications hub includes a set of biometric parameters. Each biometric parameter of the set of biometric parameters includes a preferred range. The corresponding biometric indicators are monitored using the plurality of sensors. Each biometric indicator is compared with the corresponding preferred range of the corresponding biometric indicators. A status indicia is provided when at least one of the biometric indicators falls outside the preferred range of the corresponding biometric indicators. The status indicia are delivered to a healthcare provider. The wearable member is configured to remotely receive a recommended action to be taken from the healthcare provider.

These and other aspects, objects, and features of the present invention will be understood and appreciated by those skilled in the art upon studying the following specification, claims, and appended drawings.

DETAILED DESCRIPTION OF THE PREFERRED EMBODIMENTS

Figure 1:
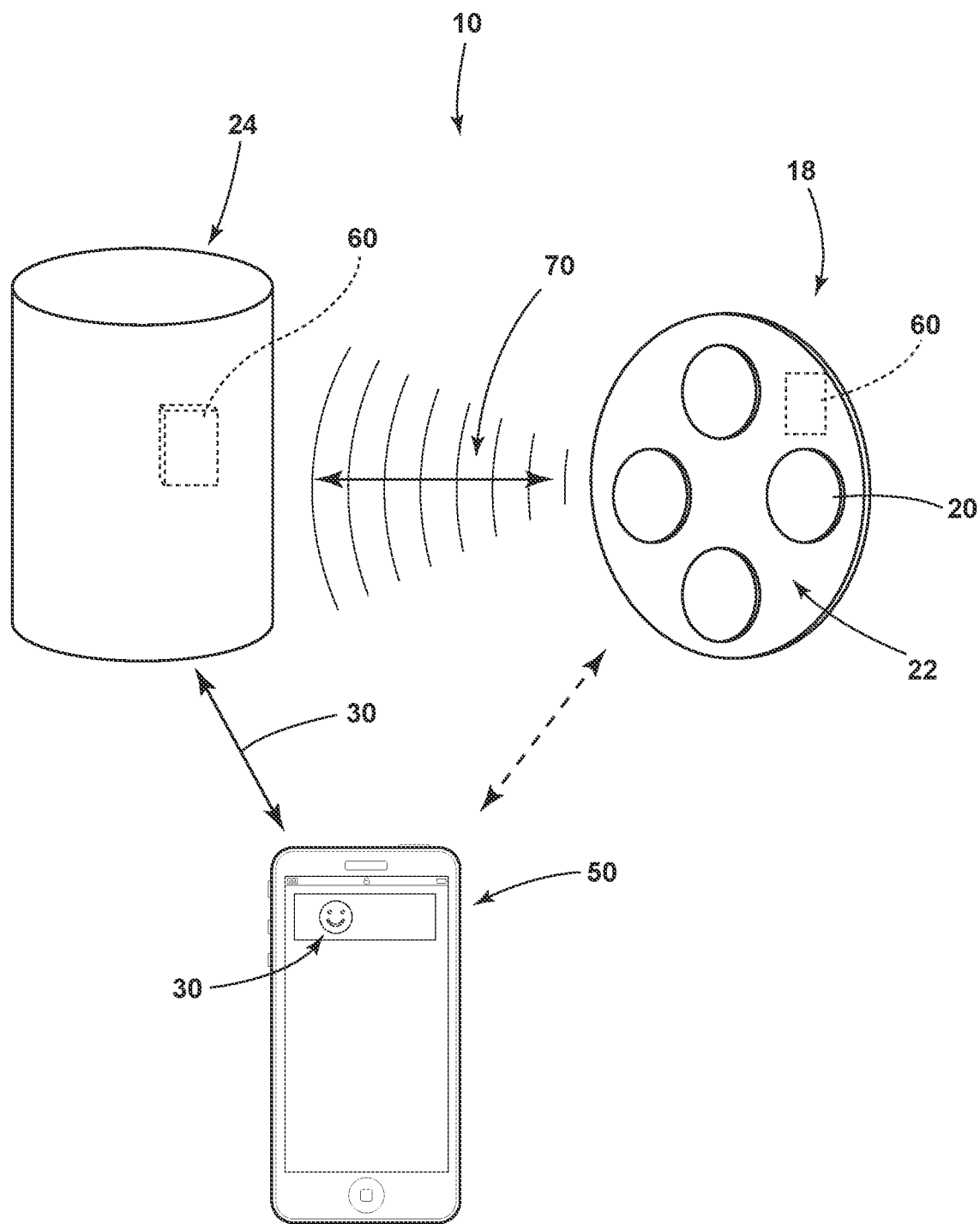
FIG. 1 is a schematic view of a hub and sensor array that are used as part of the biometric monitoring device.
Figure 2:
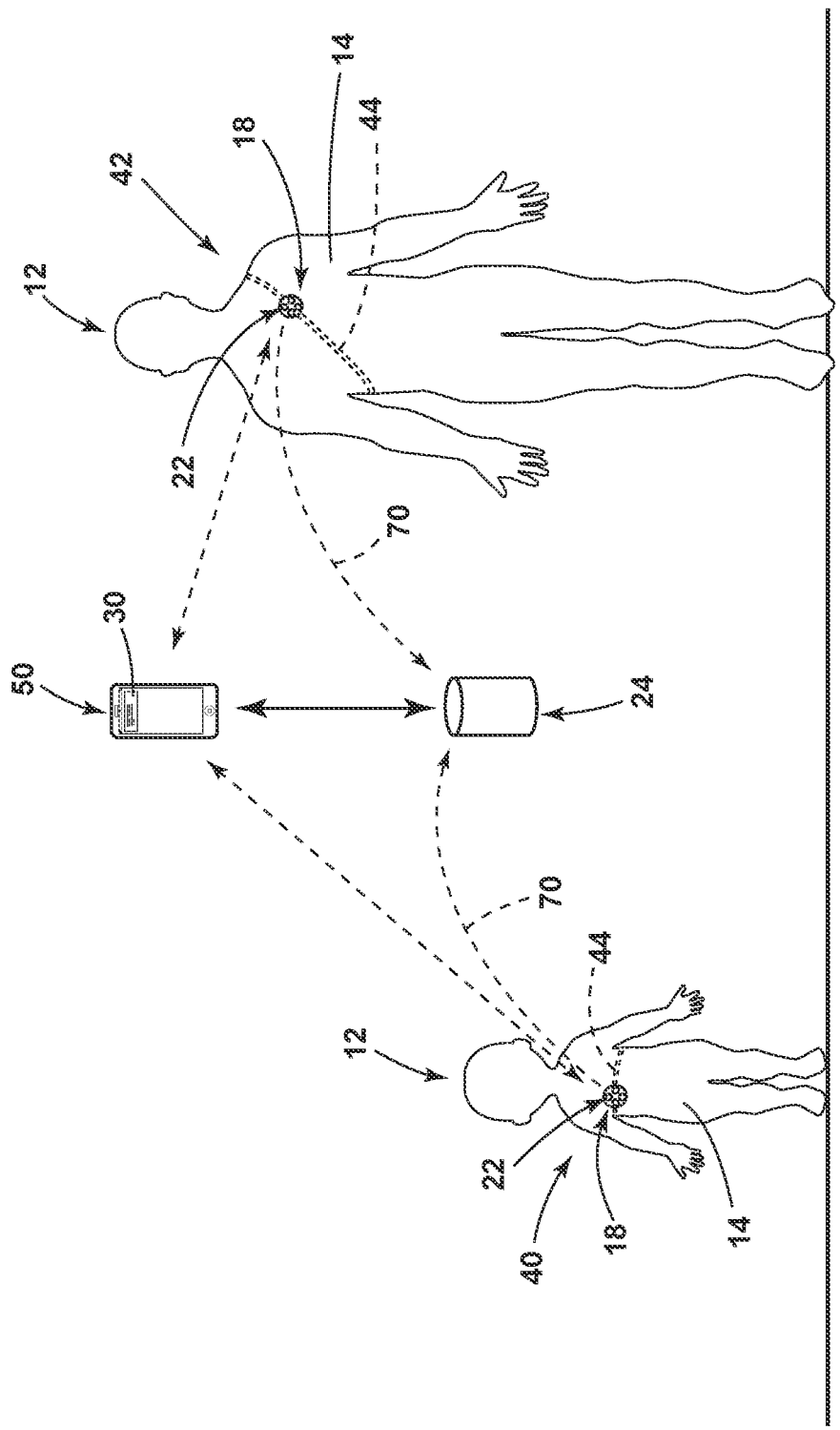
FIG. 2 is a schematic illustration of a child and an adult wearing an aspect of the sensor array, where the sensor array is in communication with the hub for the biometric monitoring device.
Figure 3:
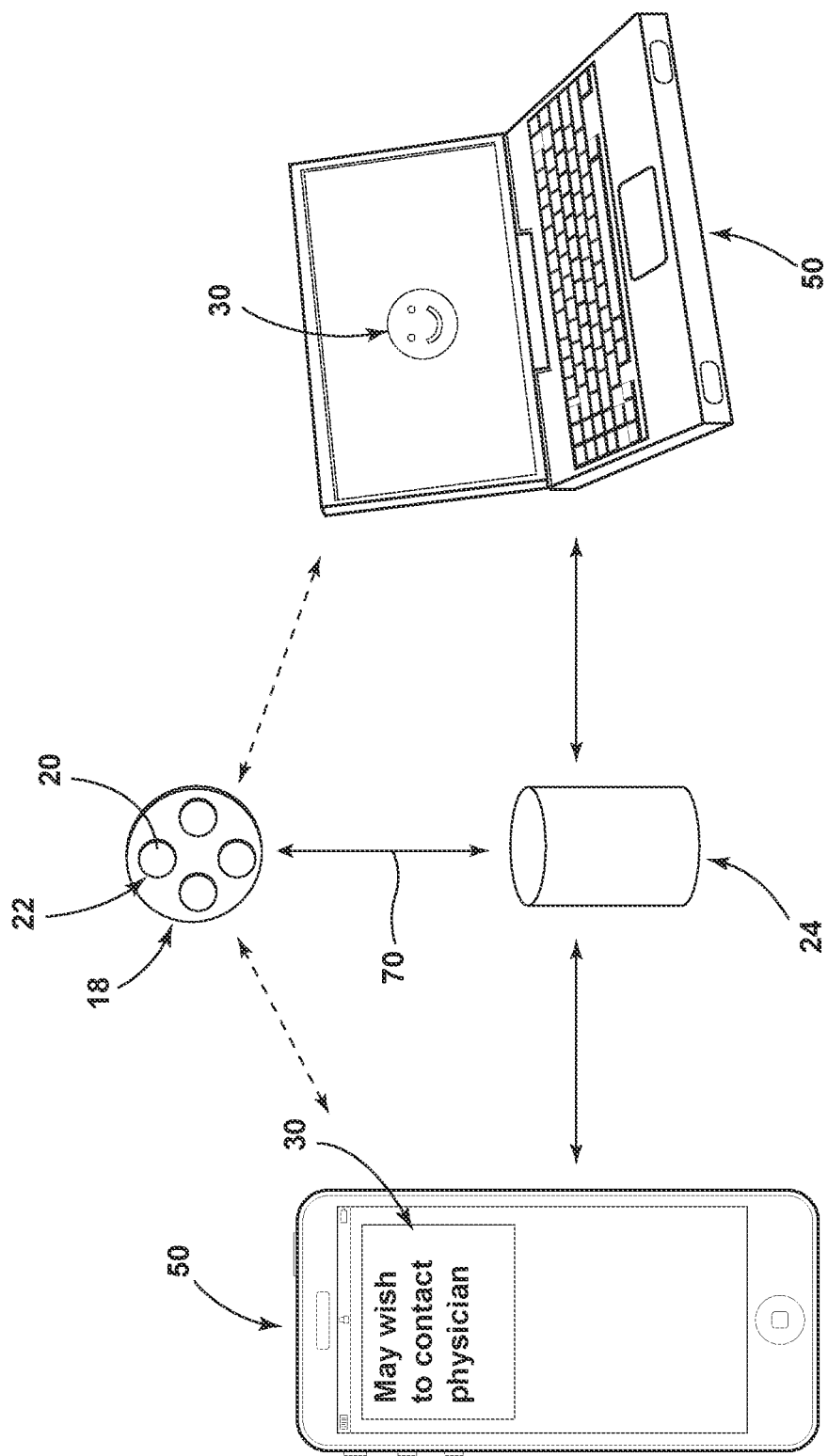
FIG. 3 is a schematic view of an aspect of the hub for the biometric monitoring device in wireless communication with a portable computing device.
Figure 4:
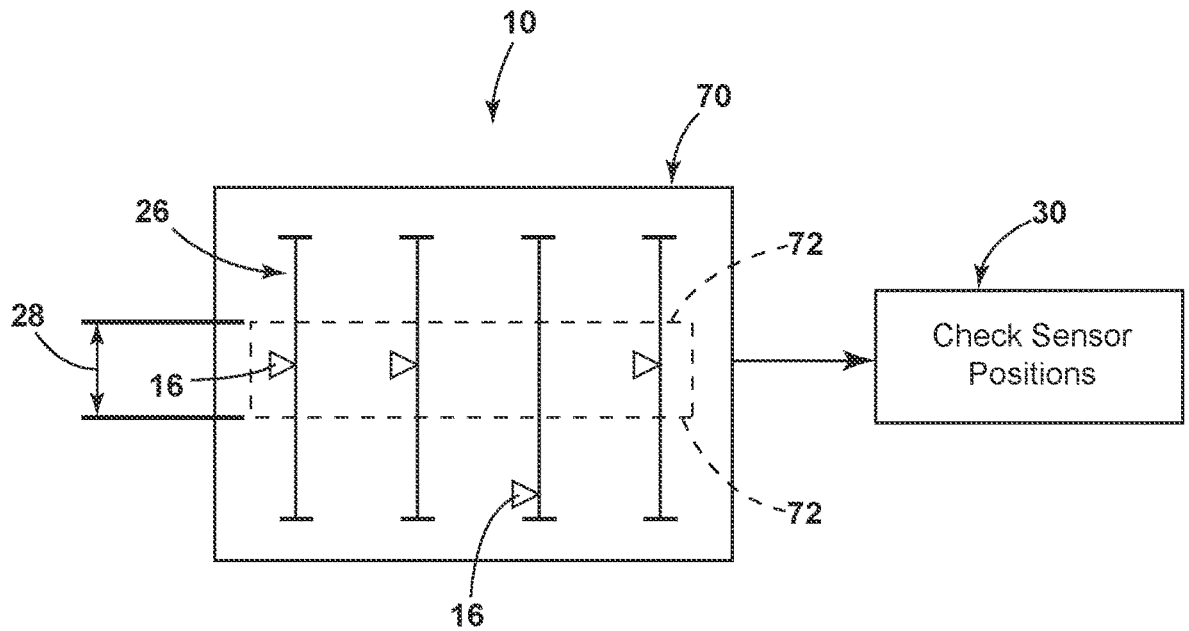
FIGS. 4-7 illustrate schematic diagrams exemplifying biometric measurements taken by the sensor array and compared with various biometric parameters saved within the biometric monitoring device, as well as indicia that are communicated by the biometric monitoring device in response to the measurements taken by the sensor array.
Figure 5:
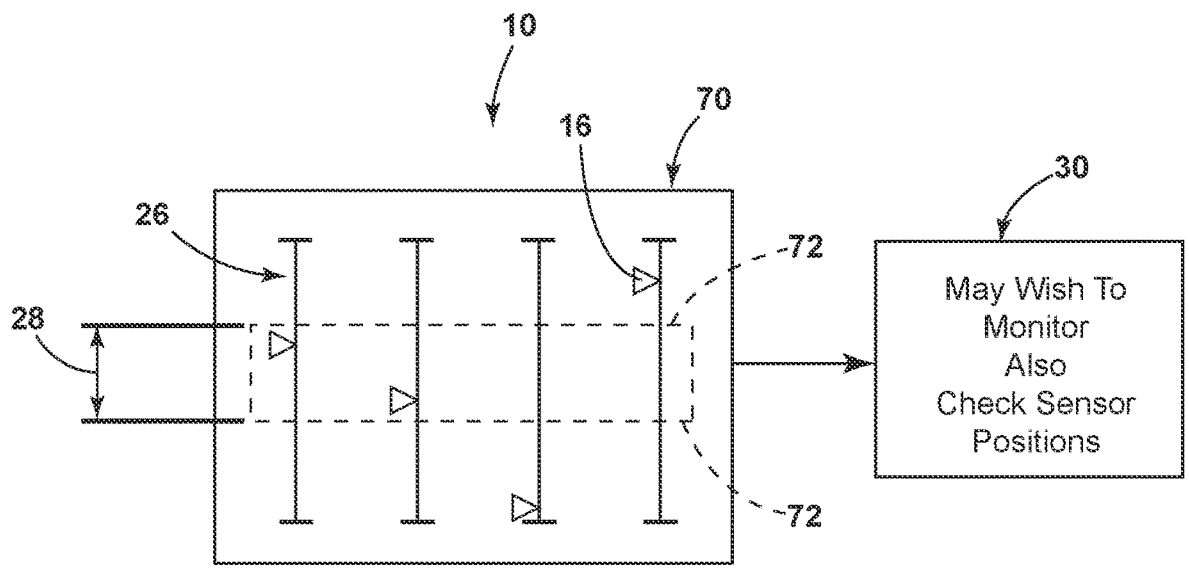
Figure 6:
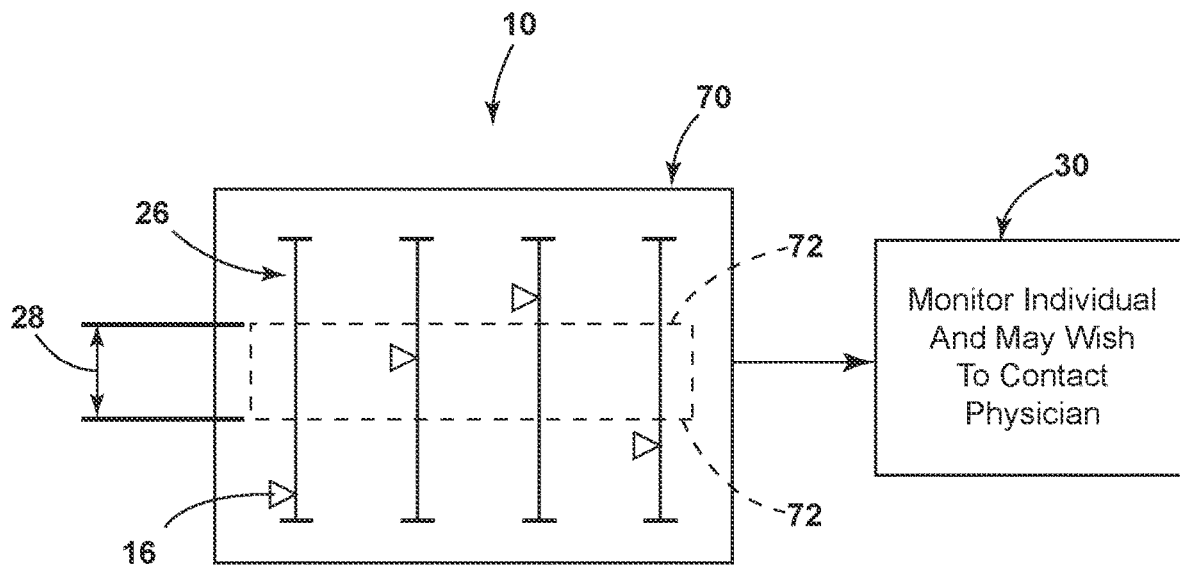
Figure 7:
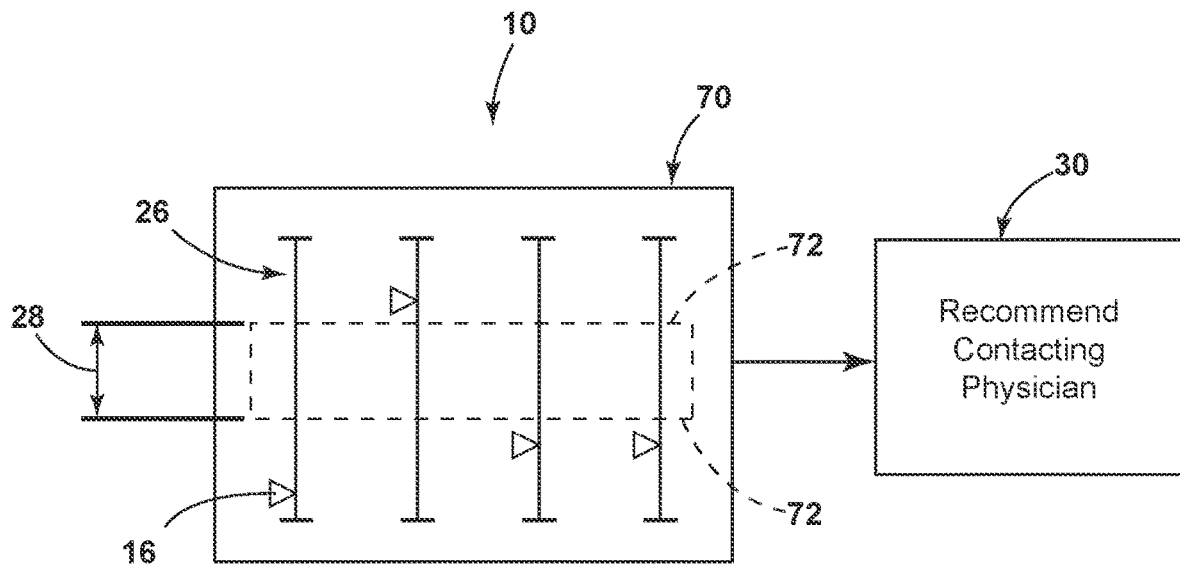
Figure 8:
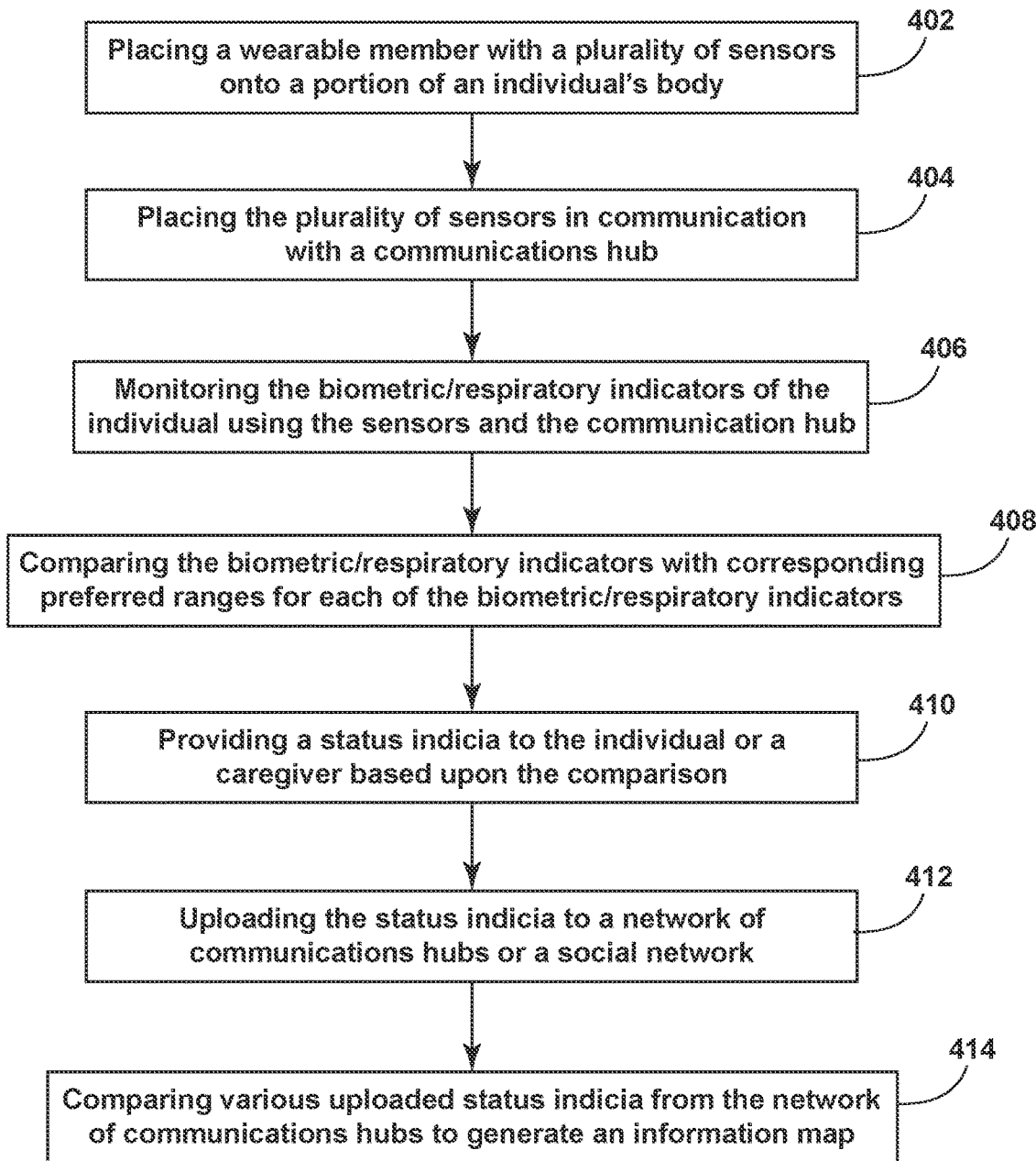
FIG. 8 is a schematic flow diagram illustrating a method for operating the biometric monitoring device.

For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

As shown in FIGS. 1-7, reference numeral 10 generally refers to a portable biometric monitor or portable health monitor that can be worn upon the body 14 of an individual 12 or proximate the individual's body 14 for measuring various biometric indicators 16 of the subject individual 12. Using these biometric indicators 16, the portable biometric monitor 10 can monitor and gather information regarding the status of an individual 12. The status of an individual 12 can be in the form of a health and/or wellness status of the individual 12. According to various aspects of the device, the portable biometric monitor 10 can include a wearable member 18 having a plurality of sensors 20 incorporated therein. The plurality of sensors 20 can be in the form of a sensor array 22 or a plurality of individual sensors 20 that are applied on or near an individual's body 14. It is contemplated that each sensor 20 of the plurality of sensors 20 is adapted to monitor a corresponding biometric indicator 16 of a plurality of biometric indicators 16. By way of example, and not limitation, the biometric indicator 16 may take the form of a respiratory indicator 16 that can provide information related to the individual's respiratory function.

According to various aspects of the device, the biometric indicators 16 can include, but are not limited to, respiratory rate, respiratory inspiratory and expiratory times and ratio, heart rate, temperature, electromyography, muscle contraction strength, electrocardiography, electroencephalography, oxygen saturation (arterial, venous, capillary), carbon dioxide level, blood pressure, hydration, glucose and electrolyte monitors, lactate level, hormone levels, bilirubin level, chemical signaling molecule levels, chemical concentration level, apnea indicators, activity level, global positioning system (GPS) data related to the body position and orientation of an individual 12 (prone vs. supine, active vs. sedentary, etc.), combinations thereof, and other various biometric indicators 16. Typically, two or more biometric indicators 16 will be utilized by the portable biometric monitor 10 in accessing the condition of the individual 12.

Referring again to FIGS. 1-7, the portable biometric monitor 10 can also include a communications hub 24 that is in selective wireless communication with at least one sensor 20 of the plurality of sensors 20. It should be understood that a wired connection between the various components of the portable biometric monitor 10 may also be implemented where desired. The communications hub 24 typically includes a processor 240 for monitoring and recording the measurements taken by the sensors 20.

During operation of the portable biometric monitor 10, at least one of the wearable member 18 and communications hub 24 can include a set of biometric parameters 26. Each corresponding biometric parameter 26 of the set of biometric parameters 26 includes a corresponding preferred range 28. Accordingly, each corresponding preferred range 28 relates to a respective and corresponding biometric indicator 16. When at least one of the sensors 20 indicates that the corresponding biometric indicator 16 is outside of the corresponding preferred range 28, the communications hub 24 may provide a status indicia 30 that corresponds to a proposed recommendation 220. It is contemplated that another component of the portable biometric monitor 10 can also display the status indicia 30. The proposed recommendation 220 can be in the form of an alert (e.g. visual, audio, haptic, tactile, combinations thereof and others) to check the status of the sensors 20 included within the wearable member 18, or can be a recommendation to take some sort of action, such as calling a healthcare provider or providing increased surveillance as to the condition of the individual 12 wearing the plurality of sensors 20. The sensors 20, communications hub 24, and portable computing device 50 may display the status indicia 30 at any point, and may alter the display if/when one or more biometric parameters 26 moves outside of the preferred range 28 and/or if the rate of change is outside of the preferred setting, all of which may result in a recommendation.

According to various aspects of the device, the preferred ranges 28 for the biometric indicators 16 may include preferred ranges 28 that correspond to current status information as well as status information over time. This status information over time may be in the form of data relating to the rates of change over time. Each of the current (or instantaneous) status information and the status information over time can be provided in real time or substantially in real time. In this manner, the sensors 20, communications hub 24, and portable computing device 50 may display the status indicia 30 at any point, and may alter the display if/when one or more biometric parameters 26 moves outside of the preferred range 28. Additionally, the status indicia 30 may be displayed when the rate of change of one or more biometric parameters 26 is outside of a preferred range 28 for the rate of change of a particular biometric parameter 26. Rate of change, according to various aspects, can be indicative of the existence of a health concern as well as the potential severity of the health concern. Accordingly, where a particular biometric parameter 26 may be within a preferred range 28, the rate of change of the biometric parameter 26 may indicate a health and/or wellness concern and may result in the communication of a recommendation. In this manner, data relating to the rate of change of a biometric parameter 26 may provide an advance status indicia 30 in the form of a recommendation, before the biometric parameter 26 actually falls outside of the preferred range 28. In certain aspects of the device, the various sensors 20 of the portable biometric monitor 10 may also, or alternatively, communicate directly with the portable computing device 50. The rate of change data and the evaluation of the biometric parameters 26 in relation to the preferred ranges 28 can be performed by a processor 240 of the sensors 20, the communications hub 24 or a portable computing device 50.

According to various aspects of the device, the portable biometric monitor 10 can be used to assist a user, a parent or other caregiver, or a healthcare monitoring entity, in making decisions regarding actions to take with respect to the individual 12. These types of recommended actions may take the form of autonomously provided actions, remotely activated recommendations or actions and other healthcare-related actions. One such recommended action can be whether or not to get a professional healthcare provider involved in caring for the individual 12 that is being monitored by the portable biometric monitor 10. These recommendations may range from a notification to the caregiver or parent or a notification to a healthcare provider or entity. The healthcare provider can include, but is not limited to, a medical or health care professional, health monitoring agencies, healthcare systems, combinations thereof and other facilities and personnel related to the provision of health care services.

In certain aspects of the device, the recommendation may take the form of a therapeutic 224 and/or medication recommendation based on the person's known medical history, and which may or may not be based on a consultation with an expert. By way of explanation, and not limitation, the presence of biometric indicators 16 being outside of a preferred range 28 may typically indicate that a recommendation is warranted. In certain individuals 12, the presence of a biometric indicator 16 outside of a preferred range 28 may be a reflection of a known or expected reaction to a prescribed medication or activity, such as when an individual diagnosed with asthma inhales albuterol, the biometric monitor 10 will typically show a fast respiratory rate and increased chest wall muscle use. In such an instance, the recommendation may take the form of a message or request to confirm that the medication was taken or the action performed.

While certain aspects of the device may be calibrated to provide a preliminary diagnosis, typically, no diagnosis is provided. Accordingly, the recommendation with respect to the actions described above is provided to encourage a user of the portable biometric monitor 10 to seek prompt and appropriate assistance of a healthcare provider so that a formal assessment and diagnosis can be made via a healthcare provider.

Referring again to FIGS. 1-7, the plurality of sensors 20 that are included within the wearable member 18 can be in the form of a sensor array 22 and can also be in the form of individual sensors 20 that can be disposed on or near the body 14 of the individual 12. The sensor array 22 can be included within a single wearable member 18 that can be attached to a portion of the user's body 14. Typical locations for placing the wearable member 18 may include, but are not limited to, near the rib cage or near the user's back so that the person cannot remove the device, such as in the case of a small child 40. More diverse locations may be possible when the portable biometric monitor 10 is used on older children and/or adults 42, who may be less likely to remove, intentionally or unintentionally, the device during use of the portable biometric monitor 10. To assist in placement of the plurality of sensors 20, the sensors 20 may be incorporated within a piece of clothing such as a shirt, onesie, or other piece of clothing. Typically, the sensors 20 will be disposed within a separate wearable member 18 that can be attached directly to the user's skin. In this manner, the sensors 20 can be in contact with the user's body 14 to provide a substantially accurate measurement of the various biometric indicators 16 that are recorded by the plurality of sensors 20. The wearable member 18 can include an adhesive or substantially tactile coating that can be at least temporarily adhered to the user's skin. Semi-permanent or permanent biometric monitoring tattoos can be printed or placed on the skin to acquire the biometric signals. Various straps 44, bands and other wrapping members can also be included as part of the wearable member 18 for coupling the plurality of sensors 20 with the user's body 14.

Referring again to FIGS. 1-7, the plurality of sensors 20 can include a wide range of sensing mechanisms that can include, but are not limited to, heart rate monitors, thermometers, EMG, EKG, EEG, I:E (inspiration:expiration) ratio monitors, oxygen saturation monitors (arterial, capillary, and/or venous), hydration monitors, lactate monitors, $CO_2$ monitors, pulse-ox monitors, hydration monitors, apnea monitors, GPS sensors for monitoring the position of an individual 12 (prone vs. supine, active vs. sedentary, etc.), combinations thereof, and other similar sensing mechanisms. Data obtained from the various sensors 20 may be stored locally, and/or transmitted to the communications hub 24 for storage, and/or transmitted to one or more portable computing devices 50 for storage, and/or ultimately transmitted to a secure data storage center. These data may be processed by a processor 240 at various events along the communication line.

According to various aspects of the device, the biometric indicators 16 measured by the plurality of sensors 20 may typically be related to respiratory indicators 16 that measure the respiratory health of the individual 12. Typically, afflictions such as bronchiolitis and other similar respiratory infections affect the respiratory function of the individual 12. Accordingly, for measuring respiratory function, the plurality of sensors 20 can include a heart rate monitor, I:E ratio monitor, body temperature thermometer and oxygen saturation monitor.

To assist in evaluating the health, such as respiratory health, of the individual 12, the corresponding preferred ranges 28 that relate to each of these sensors 20 can be predetermined based upon generally accepted biometric data 70 that relates to a typically healthy individual 12. It is also contemplated that upon acquisition of the portable biometric monitor 10, the preferred ranges 28 can be customized based upon the unique characteristics of the monitored individual 12 wearing the portable biometric monitor 10. Such unique identifying information taken during an evaluation period can include, but is not limited to, gender, gestational age, known medical conditions (e.g. asthma, COPD, heart disease, etc.), zip code or other geographical location identifying where certain afflictions may be more prominent, time of day, activity level, variation in other biometric parameters 26 and other similar information that can assist in customizing the preferred ranges 28 for the portable biometric monitor 10.

After the preferred ranges 28 of the portable biometric monitor 10 are derived, the sensors 20 can be used for measuring various biometric indicators 16 that can be relayed and compared against the preferred ranges 28. Based upon the number of biometric indicators 16 that are inside or outside of the corresponding preferred ranges 28 (or near the outer boundaries 72 of the preferred ranges 28), as well as the current value and rate of change of the biometric indicators 16, certain indicia 30 can be conveyed from the portable biometric monitor 10 to the user or caregiver of the device. By way of example, and not limitation, where a single biometric indicator 16 is outside of a corresponding preferred range 28 (illustrated in FIG. 4), such a condition may be more indicative of a mechanical issue with one of the sensors 20, rather than a legitimate health or wellness concern. Accordingly, in such an instance, the indicia 30 may be in the form of a message to at least one specifically identified person or entity, such as the user or caregiver, to verify placement of the sensors 20 or the wearable device. This indicia 30 can verify the existence of a "false positive" reading by one of the sensors 20. The indicia 30 may be also in the form of a prompt to verify the preferred ranges 28, such that an individual 12 may have a preferred range 28 different than that currently included within the portable biometric monitor 10. Predictive analytics and other statistical methods can be utilized to analyze the user's biometric indicators 16, including, but not limited to, comparing the user's current data to the user's historical trends and norms, comparing (usually anonymously) the user's data to like individuals 12, and providing estimates for likelihood of a user having a certain condition or requiring a higher level of monitoring and/or care. Algorithms and the predictive analytics and metrics may be continuously updated utilizing protected user data to refine the accuracy and appropriateness of recommendations.

Typically, various afflictions, such as respiratory illness, show symptoms across multiple systems of the body 14. Accordingly, an illness such as bronchiolitis will typically include symptoms that affect respiratory function, heart rate, temperature, and/or oxygen saturation. Accordingly, a typical affliction of bronchiolitis can correspond to multiple biometric indicators 16 being either outside of the preferred range 28 or at or near the outer boundaries 72 of the preferred ranges 28. Therefore, where a single biometric indicia 30 is outside of the corresponding preferred range 28, where the other biometric indicia 30 are well within the other corresponding preferred ranges 28, this may be indicative of a "false positive" resulting from a mechanical issue, rather than being indicative of an illness.

As further exemplified in FIGS. 4-7, where two biometric indicators 16 are outside of their corresponding preferred ranges 28 (illustrated in FIG. 5), or near the outer boundaries 72 thereof, this may be more indicative of a health concern, rather than a mechanical issue. Accordingly, where two biometric indicators 16 are outside of the corresponding preferred ranges 28, the indicia 30 provided to the user or caregiver may prompt the caregiver to provide additional monitoring to the individual 12 and also check to verify the placement of the sensors 20. Where more than two biometric indicators 16 are outside of the preferred ranges 28 or at the outer limits of the preferred ranges 28 (illustrated in FIGS. 6 and 7), this may be indicative of a potential health issue. The indicia 30 given to the user and/or caregiver may recommend that the user contact a healthcare provider. Accordingly, the user and/or caregiver can use the portable biometric monitor 10 as an early warning system as to the onset of a potential illness or respiratory affliction.

The various indicia 30 can be delivered to the user and/or the caregiver either directly via a portable computing device 50 or at the communications hub 24 or at one or more of the sensors 20. Such indicia 30 can be in the form of an illumination color of the sensor 20 and/or the communications hub 24 (e.g., green for no concern, yellow for possible concern, red for a recommended action). The indicia 30 can also be an auditory signal from the sensor 20 and/or the communications hub 24. The indicia 30 can also be delivered wirelessly via Wi-Fi; Bluetooth, or other non-transitory communication. The wireless indicia 30 can be in the form of an e-mail, text, application prompt, phone call, prompt to a wearable computing device or other similar communication to a portable computing device 50 and/or a healthcare provider. In various aspects of the device, the portable computing device 50 can take the form of any one or more of various communications and computing devices that can include, but are not limited to, smartphones, tablets, cell phones, laptop computers, desktop computers, servers, cloud computing sites, wearable computing/communications devices, portable computing assistants (Siri, Alexa, Echo, Google Home, Bixby, etc.), combinations thereof and other similar computing devices.

According to various aspects of the device, it is contemplated that the communications hub 24 may be in the form of an application, program, routine or other similar computing program that is uploaded onto and operated, at least in part, by the portable computing device 50. In such an embodiment, the communications hub 24 may be included with the portable computing device 50.

Referring again to FIGS. 1-7, it is contemplated that the portable biometric monitor 10 is a device that may be worn by the user intermittently (e.g. during an acute illness or continuously for a period of time to build a set or baseline of personalized biometric indicia 30). It is further contemplated that the portable biometric monitor 10 could be an over the counter (OTC) device that can be purchased, used for a temporary period, and then disposed of or recycled. The portable biometric monitor 10 could also be purchased over the counter and used continuously (i.e. as a wellness monitor of various biometric signals). The portable biometric monitor 10 could also be prescribed by healthcare practitioners in order to enable continuous monitoring for patients. It is also contemplated that the communications hub 24 may be a single purchase item and the plurality of sensors 20 can be an OTC purchase that is acquired and then recycled and disposed of more frequently. The communications hub 24 and/or smart device could be programmed to process either single or multiple users' data, and configured to grant passcode protected access to one or more individuals 12.

In use of the portable biometric monitor 10, at the onset of symptoms that may be indicative of a potential illness or respiratory infection, the user or caregiver can acquire the communications hub 24 and/or the plurality of sensors 20 to assist in monitoring the various biometric indicators 16 of the individual 12. It is contemplated that the wearable member 18 can be placed upon the skin of an individual 12 and can be secured thereon for multiple days or weeks to provide continuous, or substantially continuous, monitoring to monitor potential development of an infection or other illness. The portable biometric monitor 10 can be used also for monitoring secondary effects of infection such as dehydration, fever and other symptoms that are commonly associated with respiratory infections and other illnesses. It is also contemplated that the plurality of sensors 20 can include a microphone for recording various sounds, including, but not limited to, respiratory sounds and cardiac sounds. Recordings of these sounds can be delivered to a healthcare provider, and/or healthcare entity for assisting the healthcare provider in making a proper analysis and diagnosis. The information gathered by the portable biometric monitor 10 is not typically used to diagnose but can be an information gathering tool for assisting the healthcare provider in making the diagnosis.

In various aspects of the device, the portable biometric monitor 10 may include some functionality to provide and/or assist a healthcare provider in providing analysis of the biometric data. By way of example, and not limitation, the microphone can record a set of baseline recordings of breathing and cardiac sounds under various personal conditions. These baseline sounds may be compared with current sounds to assess whether any atypical or abnormal breathing sounds or cardiac sounds or rhythms are present in the breathing/cardiac patterns of the individual 12. These sounds may be assessed along with information regarding current breathing rate, heart rate and other current data and/or baseline data to assess and/or analyze whether a recommendation is appropriate.

During use of the portable biometric monitor 10, the communications hub 24 and/or the wearable member 18 can include an internal memory 60 that can be used to record the various biometric indicators 16 over time and also provide information concerning the relationship of the corresponding biometric indicators 16 in relation to the corresponding preferred ranges 28 of these indicators 16. This information can then be delivered to a healthcare provider and/or healthcare entity such as by physically delivering the internal memory 60 to the healthcare provider who can then evaluate the information. It is also contemplated that a communications hub 24 and/or the portable computing device 50 can be used to transmit, wirelessly, this biometric data 70 in real time or at periodic intervals to the healthcare provider for assisting in analysis and making a diagnosis.

Using the portable biometric monitor 10 described above, healthcare visits and healthcare costs can be greatly diminished by having a healthcare provider involved early in the potential illness. In this manner, more serious secondary effects of these illnesses may be avoided or at least mitigated. The use of the portable biometric monitor 10 may also assist healthcare providers during routine "well visits" by providing data which may identify trends 90 or concerning values which may prompt additional testing and/or diagnostic studies.

One particular illness that affects many children is bronchiolitis. Medical studies have shown that infants experienced, on average, 6-10 viral infections per year. Each of these viral infections can range from 14-28 days in duration. Accordingly, it is not uncommon for infants to have an active viral infection for approximately three to nine months of any given calendar year. Through use of the portable biometric monitor 10, these viral infections can be identified early, such that treatment can be provided for limiting the duration of these viral infections.

Bronchiolitis is a disorder commonly caused by a viral lower respiratory tract infection and is typically seen in infants less than two years old. Bronchiolitis is typically characterized by inflammation, edema, and necrosis of the epithelial cells lining the small airways within the lungs. It is also characterized by an increase in mucous production. These symptoms can lead to effects seen in respiratory function, heart rate, fever, and other health concerns.

The viruses that lead to bronchiolitis can be any one of various viruses that can include, but are not limited to, respiratory syncytial virus (RSV), rhinovirus, parainfluenza, human meta pneumovirus, influenza virus, adenovirus, coronavirus, and other identified viruses. Studies have shown that approximately 90% of children are affected by RSV by two years of age. Additionally, infection with RSV does not grant permanent or long-term immunity. In fact, studies have shown that re-infections are common throughout an individual's lifetime. Certain risk factors for more severe bronchiolitis are young age (such as less than 12 weeks), prematurity (such as less than 36 weeks gestation), congenital heart disease, chronic lung disease, cystic fibrosis, immunodeficiency, neuromuscular diseases, and airway malformation.

Additionally, while adults 42 may be able to recognize and describe abnormal physiological conditions (e.g. fast heart rate, increased respiratory rate, etc.), infants and very young children are typically unable to communicate the details of a physiological condition and/or illness. Also, certain individuals 12 (children and adults 42) may have mental or physical impairments that can also prevent communication of such conditions. Accordingly, the use of the portable biometric monitor 10 can be effective in assisting a parent or caregiver on the health of children or other individuals 12, by monitoring the biometric indicators 16 of the subject individual 12.

Once infected, bronchiolitis symptoms can include runny nose, cough, faster respiratory rate, apnea, and other respiratory distress. The presence of a normal respiratory rate suggests low risk of a significant viral or bacterial lower respiratory tract infection or pneumonia, such as a likelihood ratio of less than 0.5%. Conversely, a heightened respiratory rate such as greater than 70 breaths per minute has been associated with increased risk of severe disease, as shown in certain studies. Further, apnea was detected in 5% of children less than two years of age that were hospitalized with bronchiolitis. Also, about one in three children who have a viral infection, such as an upper respiratory tract infection, are seen to develop lower respiratory tract symptoms similar to those described herein. These symptoms in their early stages may be detectable through the use of the portable biometric monitor 10. Accordingly, a healthcare provider can be introduced and become involved in the treatment of the individual 12 before more serious symptoms may become pronounced. Additionally, where an individual 12 is shown to be more susceptible to respiratory infections, a regimen of virus prevention can be instituted in the household and can become a typical way of life. Such prevention of viral infections can include disinfecting hands before and after direct contact with patients or after contact with various objects in the vicinity of a patient, the use of alcohol-based rubs for hand decontamination when caring for children with bronchiolitis, and/or the use of soap and water. Also, avoiding smoke exposure can also be consciously limited or avoided.

The effects of bronchiolitis and other respiratory infections also go beyond the symptoms experienced by an individual 12 and their families. Bronchiolitis and similar respiratory infections in young children result in approximately 300,000 emergency room visits per year in the United States. For example, in 2002, 149,000 patients were hospitalized with bronchiolitis with an average hospital length of stay of 3.3 days. The health care cost associated with these hospitalizations resulted in a mean cost of $3,799 per hospitalization and a total cost of $543 million. Additionally, bronchiolitis, according to some studies, was shown to be the most common cause of hospitalization among infants during the first 12 months of life. The costs of hospitalizations for bronchiolitis have increased, such that over 100,000 bronchiolitis admissions occur annually in the U.S. at an estimated cost of approximately $1.73 billion. These instances of hospitalization also have patterns, such that the highest incidents of bronchiolitis occur in the cold winter months of November through April. Certain predictors can also identify a likelihood of hospitalization. As an example, premature (low gestational age) infants typically have an increased rate of hospitalization compared to the hospitalization rate than that of full term infants.

These health and economic factors can be lessened through the use of the portable biometric monitor 10 such that early identification of an illness can result in a healthcare provider being involved in the care of the individual 12 at an early stage. Treatment can also be initiated early, such that the number of hospital stays can be decreased and the length of hospital stays can also potentially be decreased.

The spread of these contagious viruses may also be diminished through the use of early monitoring that may result in the modification and behavior around more individuals 12 that may be more sensitive to viral infection.

Figure 9:
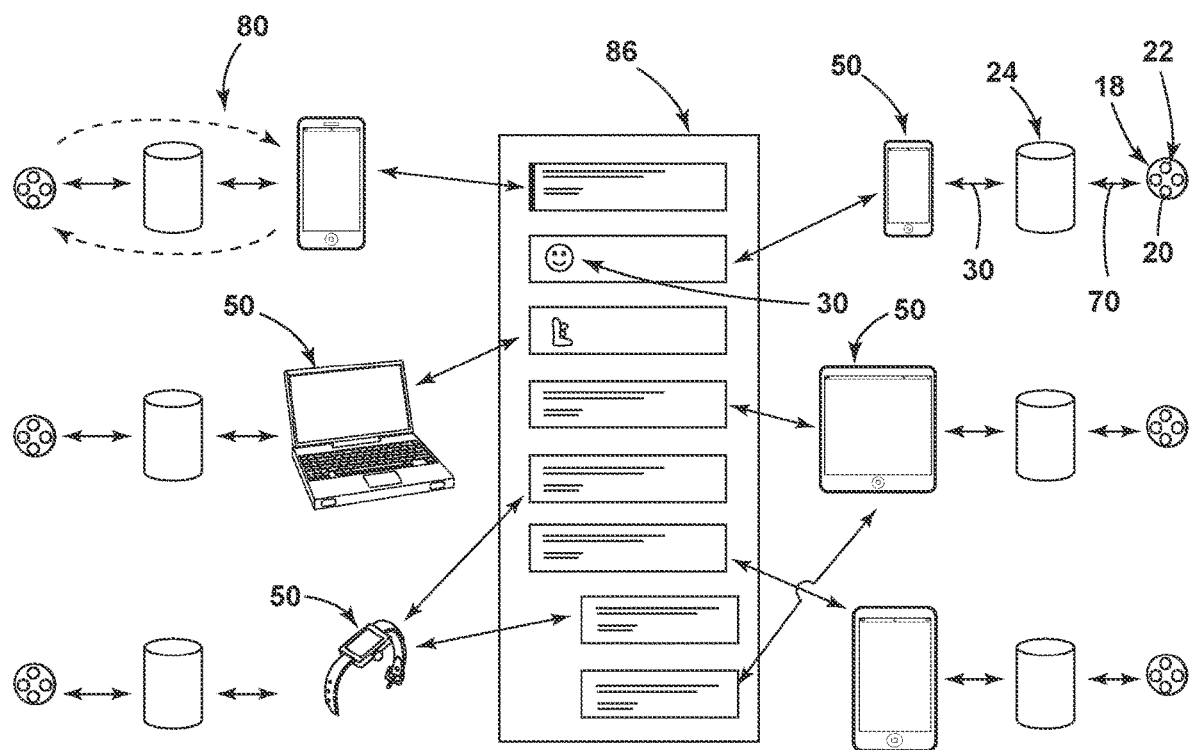
FIG. 9 is a schematic diagram illustrating an aspect of the biometric monitoring device where a user can upload various biometric markers and indicia to a social computing network.
Figure 10:
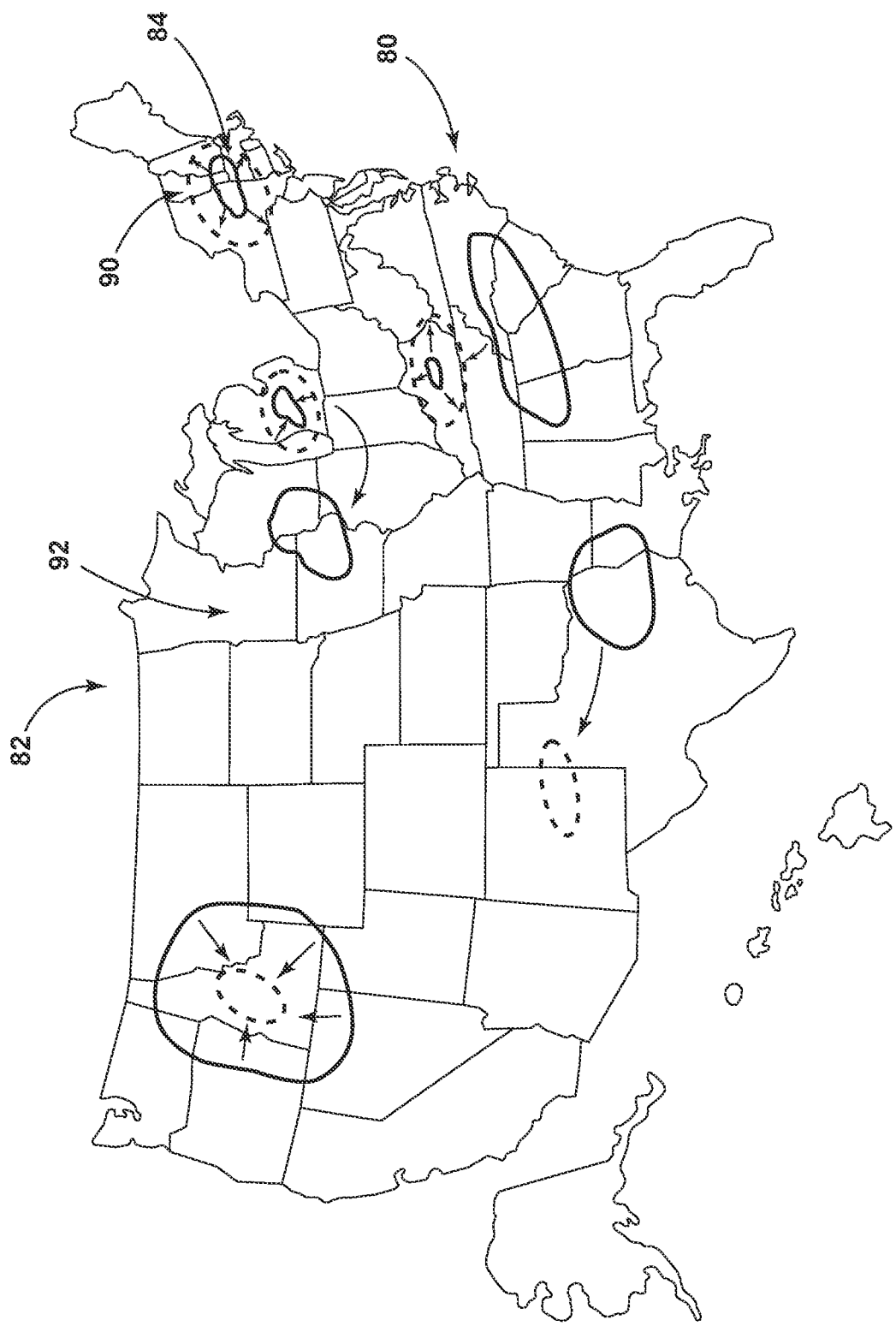
FIG. 10 is a schematic diagram illustrating a potential geographic record keeping function used in conjunction with a plurality of biometric monitoring devices.
Figure 11:
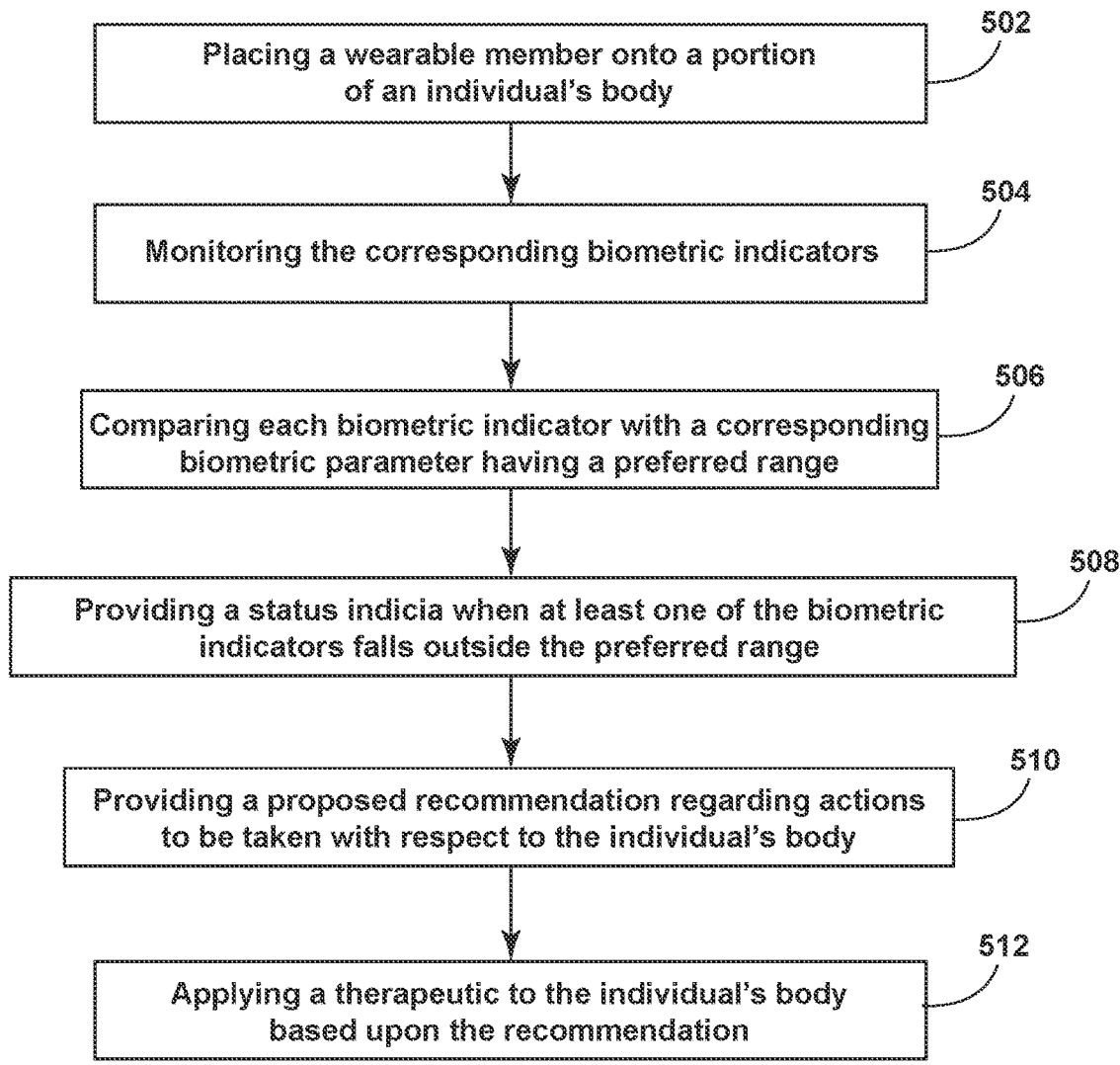
FIG. 11 is a linear flow diagram illustrating a method for providing remote healthcare based upon monitored biometric functions of an individual.

Referring now to FIGS. 9-10, it is contemplated that the use of the portable biometric monitor 10 can be conducted in conjunction with a social network 86 and other similar social cloud-based networks. Information from the communications hub 24 can be uploaded via a portable computing device 50 to a computing network that can gather various health information among multiple individuals 12. Where health disclosure laws are concerned, this information can be limited solely to the onset of an infection, such that personal identifying information can be withheld from such an upload of data. However, where voluntarily provided, a user or caregiver may wish to communicate significant information concerning the biometric data of an infection, or the onset of an infection and duration of symptoms within a particular geographic area.

A hub network 80 of portable biometric monitors 10, including a plurality of communications hubs 24 and/or a plurality of portable computing devices 50, can be used throughout a certain geographic area to monitor the presence of infections as a type of social network 86. Accordingly, data concerning viral infections can be uploaded to a social network 86 and this information can be used to provide an information or data map 82 showing trends 90 in bronchiolitis, for example, or other abnormal biometric data or illnesses at any given time. By way of example, and not limitation, data collected by a network 80 of portable biometric monitors 10, in the form of a plurality of uploaded status indicia 30, can be used to indicate that an outbreak 84 of bronchiolitis, for example, or other illness have been seen in a specific part of the country. An individual 12 wishing to travel to that portion of the country may decide to delay that trip to avoid obtaining such an infection. Travel plans can also be arranged such that travel to an unaffected area 92 when the infection rate is low can be accommodated. These trends 90 over time can also be used by hospitals and government agencies to promote habits that can limit the spread of various infections and also potentially shorten hospital stays among the population.

It is contemplated that the geographic area that can be monitored through the social network 86 in conjunction with the network 80 of portable biometric monitors 10 can vary in size. The social network 86 can be in the form of a global network, a national network, statewide network or very localized network. The social network 86 can also be configured to be scalable to adjust the size of the network 80 of portable biometric monitors 10 as needed to reflect the desired set of information. Various studies have shown that the outbreak 84 of infections within a certain geographic area can be small in nature such that a small number of counties in a particular state may be affected at a given time, while other portions of the state may be unaffected area 92 at the same time. The trends 90 in the outbreak 84 of infections can also vary over time. Accordingly, certain geographic areas may see the outbreak 84 of infection at a different time than another geographic area. Using the social network 86 in conjunction with the network 80 of portable biometric monitors 10, these trends 90 of outbreaks 84 and unaffected areas 92 over time can be recorded and evaluated over time and patterns can be generated to assist healthcare providers in planning for these regular onsets of infection. In this manner, hospitals can use a more proactive approach in assisting the public in recognizing and treating these infections to limit their effects on individuals 12 and families and also the financial effects on the healthcare system at large.

Referring now to FIGS. 1-10, having described various aspects of the device, a method 400 is disclosed for monitoring the biometric function of an individual 12. The method 400 can include steps of placing a wearable member 18 onto a portion of an individual's body 14 (step 402). As discussed previously, a plurality of sensors 20 within the wearable member 18 are positioned to monitor corresponding biometric indicators 16, such as respiratory indicators 16.

Once the wearable member 18 is placed onto a portion of the individual's body 14, the plurality of sensors 20 can be placed in wireless communication at least with a communications hub 24 (step 404). Wireless communication can also be established between the sensors 20 and one or more portable computing devices 50. The communications hub 24 and/or the wearable member 18 include a set of respiratory parameters 26 or biometric parameters 26, wherein each respiratory parameter 26 of the set of respiratory parameters 26 includes a preferred range 28. This information may also be stored within the portable computing device 50. As discussed previously, this preferred range 28 can be based upon a set of generally accepted ranges indicative of a "healthy" individual 12. These parameters 26 can also be contoured and customized based upon information gathered about the individual 12 being monitored. The corresponding biometric indicators 16 can then be monitored by the plurality of sensors 20 (step 406). These biometric indicators 16 can then be compared with the corresponding preferred ranges 28 of the corresponding biometric indicators 16 (step 408). As discussed previously, depending upon the number of biometric indicators 16 that are within and outside the respective preferred ranges 28, and the position of the indicators 16 within each of the respective preferred ranges 28, various indicia 30 can be provided to the user and/or caregiver. A status indicia 30 can then be provided to the individual 12 and/or caregiver (step 410). The status indicia 30 can be provided periodically regardless of the position of the biometric indicator 16 within the corresponding preferred range 28. In this manner, where the biometric indicators 16 are all well within the preferred ranges 28, the indicia 30 can be in the form of a healthy symbol, various emojis, or other similar indicia 30 indicative of a biometric indicia 30 being within the preferred parameters 26. This instance can also be communicated through the absence of an indicia 30.

Typically, some indicia 30 will be provided such that the user or caregiver understands that the portable biometric monitor 10 is operational and is monitoring the biometric indicators 16 and respiratory indicators 16 of the individual 12. Conversely, as discussed above, various indicators 16 can be provided when one or more of the respiratory indicators 16 or biometric indicators 16 falls outside of the preferred ranges 28 or moves toward the outer boundaries 72 of the preferred ranges 28 for the corresponding preferred range 28. Again, these indicia 30 can be in the form of a prompt to verify the placement of the sensors 20, to increase monitoring of the individual 12, or to contact a healthcare provider so that a proper diagnosis can be made.

According to the method 400, the status indicia 30 can then be uploaded to a network 80 (step 412). In such an embodiment, the status indicia 30 is selectively shareable with a network 80 of communication hubs 24 as well as portable computing devices 50 and, in turn, the social network 86. This status indicia 30 and recorded data can also be uploaded to be accessed by a healthcare provider. In this manner, the healthcare provider can analyze the recorded data and can provide additional information concerning actions that should be taken by the individual 12 and/or the healthcare provider.

By way of example, and not limitation, where data is provided to a healthcare provider, a healthcare provider can observe the data over time and may be able to provide periodic checkups to the individual 12 such that the healthcare provider can recommend a specific action and/or testing, or that the individual 12 be brought into a hospital or other healthcare facility. In this manner, the healthcare provider may be able to provide virtual "house calls" without leaving the hospital or their office. These virtual "house calls" may have significant advantages over conventional telehealth modalities. The virtual "house calls" that can be performed using the portable biometric monitor 10 can provide a healthcare provider with various and current biometric data 70 that can be immediately available for analysis. This real time or substantially real time provision of biometric data 70 can enable clinicians to more accurately identify current abnormal biometric values which, in turn, can aid in diagnosis and prompt recognition of disease severity and trajectory.

According to the method 400, these uploaded status indicia 30 can be compared with other status indicia 30 throughout the network 80 of communications hubs 24 and various information plots and information maps 82 can be generated (step 414). These information maps 82, as discussed above, can be used by individuals 12 for planning travel, by hospitals for planning corrective steps to deal with various infections that may have cyclical or geographic patterns, and also assisting various entities in communicating to a particular community that an infection trend 90 is occurring or is imminent.

According to the various embodiments, the portable biometric monitor 10 can be an OTC device that can be used by an individual 12 to monitor the biometric indicators 16 of an individual 12 that may show signs of a respiratory illness or other infection or illness. The device may also be used by hospitals to provide care for individuals 12 such that individuals' biometric indicators 16 can be communicated to a central station for monitoring by one or more healthcare providers. In the case of the portable biometric monitor 10 being used with a hospital, the portable biometric monitor 10 may be used to provide data to a healthcare provider for making the diagnosis and/or identifying the disease severity and trajectory with respect to an in-patient community of individuals 12. The wireless communication functions of the portable biometric monitor 10 can also be used to provide accurate and real time outpatient monitoring by a healthcare provider of one or more individuals 12.

The use of the portable biometric monitor 10 can be implemented to allow for monitoring of multiple individuals 12 to limit healthcare costs associated with frequent visits by individuals 12 that may not require in-person treatment. Conversely, an individual 12 who is showing signs of an illness may use the portable biometric monitor 10 to receive a recommendation to go see a healthcare provider to receive early recognition and treatment to prevent a hospital stay or limit the time period of a hospital stay. The use of a portable biometric monitor 10 can decrease healthcare costs and provide an effective tool for early treatment of various infections and/or illnesses that may be preventable and also may be lessened in severity due to early identification of treatment.

Referring now to FIGS. 1-12, the portable biometric monitor 10 can be used as part of a portable biometric healthcare interface 210 for providing remote healthcare. This remote healthcare can be provided based upon the monitored biometric functions of the individual 12 having the wearable member 18 on their body 14. In this manner, the portable biometric monitor 10, as discussed herein, utilizes various sensors 20 for monitoring the various biometric indicators 16 of the individual 12. The term remote health care can include, but should not be limited to, in-home health care, autonomous healthcare management, remote healthcare management, combinations thereof and other forms of remote care that can be provided using aspects of the portable biometric monitor 10.

Referring again to FIGS. 1-12, the healthcare interface 210 includes the wearable member 18 that includes the plurality of sensors 20 that are incorporated within the wearable member 18. Each sensor 20 is adapted to monitor at least one corresponding biometric indicator 16. As discussed herein, a communications hub 24 is in communication with a plurality of sensors 20. In certain aspects of the device, the communications hub 24 is incorporated within the wearable member 18 such that the wearable member 18 having a plurality of sensors 20 and the communications hub 24 defines the self-contained device that acts as the healthcare interface 210, as will be described more fully below.

Referring again to FIGS. 1-12, the wearable member 18 and the communications hub 24 cooperatively include a set of biometric parameters 26. Each biometric parameter 26 of the set of biometric parameters 26 includes a corresponding preferred range 28. At least one of the sensors 20 in combination with the processor 240 is configured to indicate when one or more of the corresponding biometric indicators 16 is outside of the corresponding preferred range 28. In such an instance, the communications hub 24 provides status indicia 30 corresponding to a proposed recommendation 220. This proposed recommendation 220 can be in the form of a proposed remedial action 222.

According to various aspects of the device, this proposed remedial action 222 can include a recommendation that the individual 12 be given certain therapeutic 224 or treatments, or certain therapeutics 224 or treatments be applied to the body 14 of the individual 12. In certain aspects of the device, the remedial action 222 to be taken can include a wearable member 18 directly applying a therapeutic 224, typically in the form of at least one of a topical therapeutic, transdermal therapeutic, optic therapeutic, otic therapeutic, or other similar therapeutic remedy directly to the body 14 of the individual 12. In such an embodiment, the wearable member 18 can include an applicator 226 that is coupled to a processor 240.

It is also contemplated that the wearable member 18 can be used in combination with one or more exogenous devices. In such an aspect of the device, the wearable member 18 can communicate with a separate applicator or delivery device to initiate, modify or stop the delivery or application of a topical therapeutic, transdermal therapeutic, optic therapeutic, otic therapeutic, or other similar therapeutic remedy directly to the body 14 of the individual 12. This can be in the form of an intravenous drip, a separate applicator, or other similar applicator or delivery device. The wearable member can also cooperate with other devices by recommending usage of one or more exogenous devices, such as inhalers, oral or anal medications, drops, or other similar devices and dosing mechanisms and methods. In this manner, the remedial treatments and therapeutics 224 can be directly applied by the wearable member 18. In addition, the wearable member 18 can be used to apply additional diagnostics, therapeutics and/or recommendations as well as performing these functions in a cooperative fashion through a separate wearable device or separate exogenous device.

Figure 12:
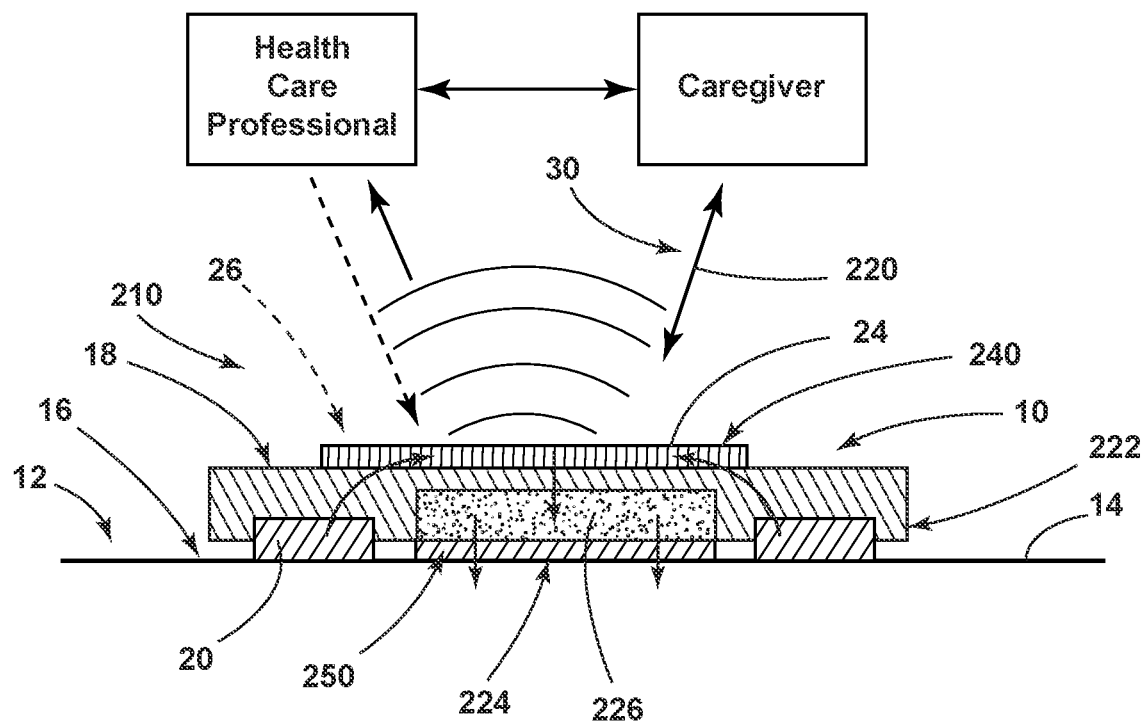
FIG. 12 is a schematic cross-sectional view of an aspect of the wearable member placed on an individual's body and incorporating an applicator for directly applying remedial treatments.

As exemplified in FIG. 12, the wearable member 18 can include a processor 240 which cooperates with the sensors 20 to monitor the biometric parameters 26 in relation to the corresponding preferred ranges 28 of the healthcare interface 210. Using these monitored biometric parameters 26, the healthcare interface 210 can provide a proposed recommendation 220 regarding actions to be taken with respect to the body 14 of the individual 12. As discussed above, these actions can be in the form of remedial actions 222, as discussed herein. These remedial actions 222 can include, but are not limited to, a recommendation to check the status of the wearable member 18 and the sensors 20, a recommendation to contact a healthcare professional, a recommendation to closely monitor the individual 12, a recommendation to apply the therapeutic 224, as discussed herein, and other similar recommendations. As discussed herein, these remedial actions can be performed by the wearable member 18 directly or in cooperation with a separate wearable device or separate exogenous device.

Referring again to FIGS. 1-12, the plurality of sensors 20, and the communications hub 24 cooperate to detect an absolute change (positive or negative), in relation to a baseline value of a biometric indicator 16. These absolute changes can also be with regard to a rate of change or a pattern of changes with respect to a value representing the one or more biometric indicators 16. These absolute changes can be in the form of changes with respect to temperature, heart rate, respiratory rate, chest wall movement, electrolytes of perspiration, blood and/or tissue, or other similar biometric changes. The plurality of sensors 20, the communications hub 24 and the processor 240 cooperate to determine whether these absolute changes are consistent with a change in the health of the individual 12 that may require remedial action 222. In various aspects, the communications hub 24 and the processor 240 can include various parameters 26 that may be indicative of a particular change in health, or various medical conditions, as discussed herein. The healthcare interface 210 that includes the wearable member 18 analyzes these absolute changes from the baseline value of one or more biometric indicators 16. If consistent with the set of possible diagnosis or conditions, a proposed recommendation 220 may be provided by the healthcare interface 210 for a healthcare provider to apply a therapeutic 224 or other home-based intervention, as discussed herein. The healthcare interface 210 can also be used by the healthcare provider to initiate, perform or otherwise conduct additional ancillary or confirmatory diagnostic tests as well as obtain, monitor and review corresponding responses.

In certain aspects of the device, as exemplified in FIG. 12, the wearable member 18 can include the applicator 226 that provides for a system to provide the therapeutic 224 or other medication directly through the wearable member 18 and onto and/or into the body 14 of the individual 12. This instruction for activating the applicator 226 can be provided directly on the wearable member 18 or can be engaged, wirelessly, through a portable computing device 50 of the caregiver. The applicator 226 can be used to apply a medical treatment onto a surface of the body 14 of the individual 12 as well as into the body 14 of the individual 12. Such dosing or delivery of the medical treatment can be conducted through routes that can include, but are not limited to, transcutaneous, transdermal, subcutaneous, otic, oral, rectal, inhaled, intravenous combinations thereof and other similar delivery methods.

It is also contemplated that a healthcare professional can remotely activate the applicator 226 to provide certain therapeutics 224, medication or topical treatment to the body 14 of the individual 12, via the wearable member 18. As described herein, the term therapeutic 224 can be in the form of any one of various actions that can be administered by or through the wearable member 18. These therapeutics can include, but are not limited to the administration of a delivered or dosed medical treatment, diagnostic, evaluation or other similar action that can be taken through the use of the wearable member 18.

In certain aspects of the device, the healthcare professional can activate the applicator 226 after notifying a caregiver and receiving authorization from the caregiver to activate the applicator 226. This sequence of events can provide for a full disclosure of medical care to authorized members of the care team of the individual 12, particularly in the case of infants, minors, and other individuals 12 with diminished capacity for making healthcare decisions.

Through the wearable member 18, paths of communication can be provided between the healthcare professional, the caregiver and other healthcare providers and healthcare facilities. In this manner, members of the health care team for the individual 12 can communicate with one another using the wearable member 18 as a communications interface. Through this communication network provided using the wearable member 18, open lines of communication can be formed and utilized for monitoring, diagnosing and treating an individual 12. As discussed herein, the wearable member 18 can also be used to perform or initiate the performance of certain therapies and/or diagnostics. The therapies and diagnostics may be conducted via an apparatus that is incorporated within the wearable member 18, such as through the application 226 or the sensors 20. The therapies and diagnostics can also be conducted via a separate wearable device or separate exogenous device.

Referring again to FIG. 12, the wearable member 18 can include the plurality of sensors 20 and the applicator 226 incorporated therein. The processor 240 can be used for providing communication between the communications hub 24 and the plurality of sensors 20. The processor 240 and the communications hub 24 can also be used for providing communication between the wearable member 18 and the caregiver, as well as, where desired, the communication between the healthcare professional and the wearable member 18. It is contemplated that the communications hub 24 can also provide a communications interface between the healthcare professional and the caregiver. These communications can be encrypted through the use of the communications hub 24 to provide a secure communications interface between a caregiver and a healthcare professional. Through this secure healthcare interface 210, proposed communications and remedial actions 222 can be provided to at least one specifically identified individual 12. These communications can include communications to emergency services such as ambulances, hospitals, emergency rooms. urgent care facilities, acute care facilities and other quick-response healthcare facilities.

Referring again to FIG. 11, having described various aspects of the interface, a method 500 is disclosed for providing remote healthcare based upon one or more monitored biometric indicators 16 of an individual 12. According to the method 500, a step 502 includes placing a wearable member 18 onto a portion of the body 14 of the individual 12. The plurality of sensors 20 within the wearable member 18 are positioned to monitor corresponding biometric indicators 16. After placing the wearable member 18, the corresponding biometric indicators 16 are monitored using the plurality of sensors 20 (step 504). Each biometric indicator 16 is compared with a corresponding biometric parameter 26 (step 506). Each corresponding biometric parameter 26 includes a corresponding preferred range 28. A status indicia 30 is provided when at least one of the biometric indicators 16 falls outside of the preferred range 28 of the corresponding biometric indicators 16 (step 508). A proposed recommendation 220 is provided regarding actions to be taken with respect to the body 14 of the individual 12 (step 510). According to step 512, these actions can include using the wearable member 18 to directly apply or otherwise administer at least one of various therapeutics 224 (step 512). These therapeutics 224 can include a topical therapeutic, transdermal therapeutic, optic therapeutic, otic therapeutic and other similar therapeutics and remedial treatments. In general, the therapeutics 224 can be in the form of remedial actions 222, diagnostics, recommendations, actions taken by the wearable member 18, actions taken by a separate device, combinations thereof, and other similar activities. As discussed above, the applicator 226 of the wearable member 18 can be used for providing these treatments and remedial therapeutics 224 directly to the body 14 of the individual 12.

It is contemplated that the wearable member 18 can be used to facilitate various recommendations and actions with respect to the remedial actions 222 described herein. These recommendations and actions can be directed to the performance or facilitation of a particular diagnostic action. Such diagnostic action can be performed by the wearable member 18 or can be facilitated through a separate mechanism. The results of such diagnostic action can be communicated via the wearable member 18 and/or the communications hub 24, similar to other recommendations that are described herein. Also, the wearable member 18 can be used to facilitate the administration or application of a particular therapeutic 224, as discussed herein. The administration of the therapeutic 224 can be administered through the wearable member 18 or can be facilitated through a separate mechanism, service or healthcare provider. Accordingly, the wearable member 18 can provide recommendations regarding diagnostics and therapeutics 224 that the wearer or caregiver can consider for future performance or administration. In certain instances, the wearable member 18 can directly perform the diagnostic or administer the therapeutic 224 relative the individual 12. In addition, the wearable member 18 can be used to communicate with a healthcare facility to obtain orders for diagnostics and prescriptions for therapeutics.

As discussed above, the applying of therapeutics 224 according to step 512 can include such remedial action 222 being taken remotely and initiated by a healthcare provider to activate an interface portion 250 of the wearable member 18, where the interface portion 250 can include the applicator 226.

In a specific exemplary aspect of the device, the wearable member 18 and the sensors 20 incorporated therein can be used to detect an abnormal level of bilirubin within an infant having the wearable member 18 positioned on their body 14. The healthcare interface 210, after detecting this biometric indicator 16 as being outside of the corresponding preferred range 28, can recommend that the infant be exposed to a system to lower the level of bilirubin. A corresponding remedial action 222 provided by the wearable member 18 can include a recommendation to position a phototherapy device or wearable device for a certain length of time. Where such a diagnosis is made by a healthcare professional, a phototherapy device can be attached to the wearable member 18 to be activated at appropriate times based upon the biometric indicators 16 in relation to the corresponding preferred ranges 28 of the biometric indicators 16. Such an activation could be made automatically based upon the readings of the plurality of sensors 20 and a comparison of the readings within the processor 240 in relation to the corresponding preferred ranges 28 of the biometric indicators 16. In addition, the activation of the remedial action 222 can be made remotely by a healthcare professional or caregiver. It is contemplated that the phototherapy device and other separate or exogenous device can be coupled with the wearable member 18 through a wired connection or can be wirelessly connected to the wearable member 18.

In certain aspects of the device, the remedial action 222 that is recommended via the wearable member 18 can include recommendations to provide additional feedings for providing additional fluids to ensure hydration. The remedial action 222 can include any one or more of various actions that can include, but are not limited to, actions and functions that can be initiated, modulated or stopped to achieve the desired effect by actions including, but not limited to, turning the therapy on or off, increasing or decreasing the intensity and or duration of the therapy, and monitoring for effects of the subject therapy or combination of therapies.

In regard to older patients or patients having specific heart conditions or other specifically identifiable conditions, certain condition-specific remedial actions 222 can be recommended or provided. In the case of a patient at risk of heart attacks, nitroglycerin may be provided as a therapeutic 224 by the wearable member 18, or a recommendation to provide nitroglycerin can be provided by the wearable member 18. In addition, in certain aspects of the device, the wearable member 18 can be fitted with an on-board electrical device that can perform cardioversion or defibrillation in the event of a cardiac event.

Using the wearable member 18, it is typical that the applicator 226 will be used to provide over-the-counter type treatments, where such treatments may not need to be directly or closely monitored by a healthcare professional. It is contemplated that other prescription-type treatments and medications can be provided. In such a condition, the processor 240, the communications hub 24 and the applicator 226 can cooperate so that certain oversight can be provided by a healthcare professional in relation to the use of such prescription medications and treatments.

In certain severe or extreme conditions, the wearable member 18 can be used to provide a remedial action 222 in response to serious healthcare conditions. In certain aspects of the device, the absolute change in the value of one or more biometric indicators 16, rates of change of the biometric indicators 16, or pattern of changes in the biometric indicators 16 can be consistent with a severe change in health of the individual 12. In these instances, the healthcare interface 210 can provide an alert that an individual 12 is in distress or needs assistance. This alert can be in any one or more of various forms, such as, but not limited to, audible, visual, haptic, tactile, graphic, digital, combinations thereof and other similar alerts. It is also contemplated that the wearable member 18 can provide a status indicia 30 or other communication to a caregiver, as well as a healthcare professional, that an individual 12 is in distress or needs immediate attention.

By way of example, and not limitation, the wearable member 18, in the case of a severe change in the value of biometric indicators 16, can instruct an individual 12 to call 911 or other emergency service. A status indicia 30 or other communication can be provided directly to a healthcare professional that emergency intervention is required with respect to the individual 12. In certain aspects of the device, the wearable member 18 can directly contact emergency medical services as well as healthcare providers, caregivers, and other individuals 12 needed for an emergency healthcare episode.

Figure 13:
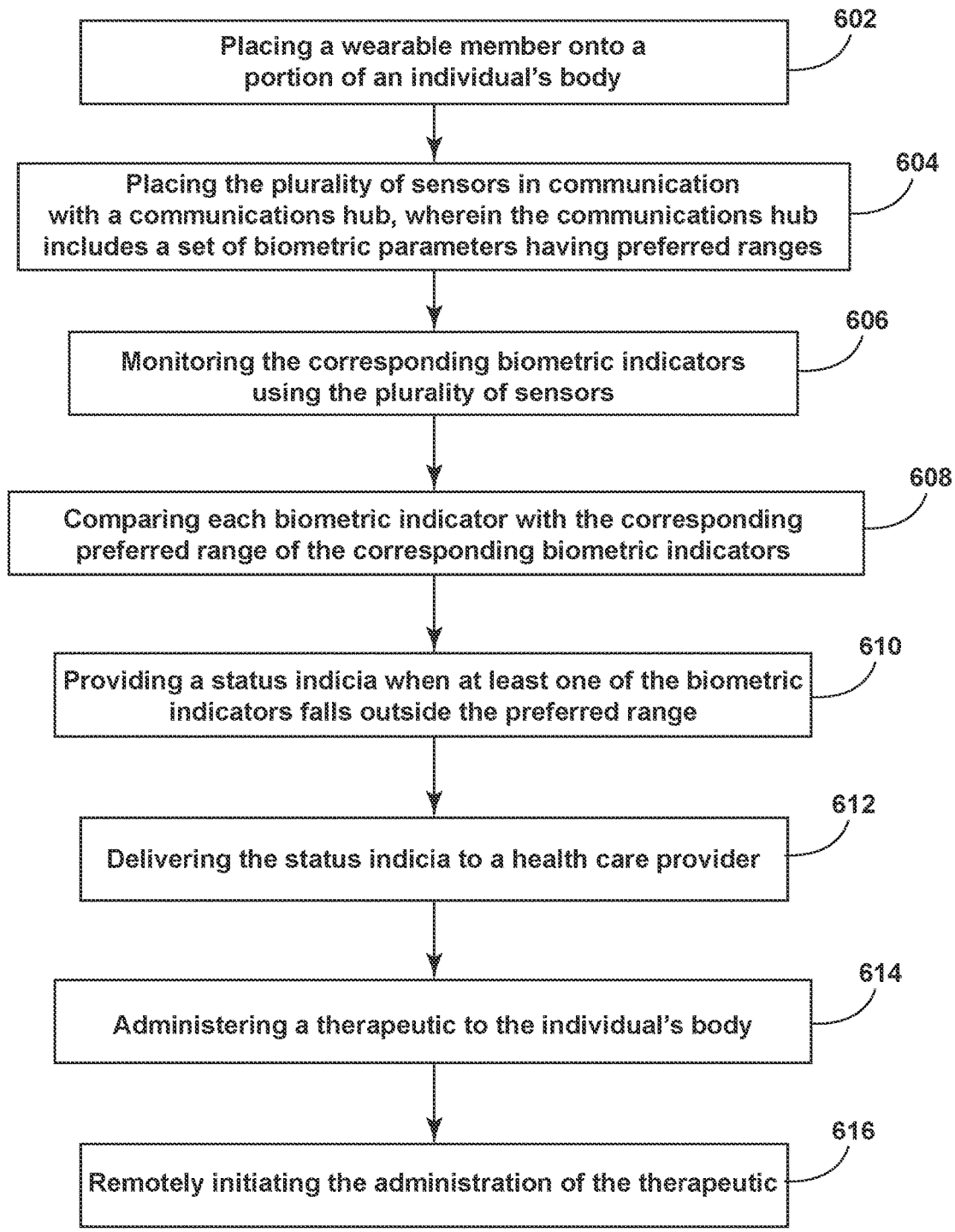
FIG. 13 is a linear flow diagram illustrating a method for providing remote healthcare based upon monitored biometric functions of an individual.

Referring now to FIG. 13, having described various aspects of the healthcare interface 210, a method 600 is included for providing remote healthcare based upon one or more monitored biometric indicators 16 of an individual 12. According to the method 600, a wearable member 18 is placed onto a portion of the body 14 of the individual 12 (step 602). A plurality of sensors 20 of the wearable member 18 are positioned to monitor corresponding biometric indicators 16. The plurality of sensors 20 are placed in communication with a communications hub 24 (step 604). It is contemplated that the communications hub 24 includes a set of biometric parameters 26 and each biometric parameter 26 of the set of biometric parameters 26 includes a preferred range 28. As discussed above, it is contemplated that the communications hub 24 can be incorporated within the wearable member 18, or be a separate component of the healthcare interface 210. The corresponding biometric indicators 16 are monitored using a plurality of sensors 20 (step 606). Each biometric indicator 16 is compared within the corresponding preferred ranges 28 of the corresponding biometric indicators 16 (step 608). A status indicia 30 is provided when at least one of the biometric indicators 16 falls outside of the preferred range 28 of the corresponding biometric indicators 16 (step 610). The status indicia 30 is then delivered to a healthcare provider (step 612). The wearable member 18 is configured to remotely receive a recommended action to be taken from the healthcare provider. According to the method 600, the recommended action to be taken includes the wearable member 18 directly applying and/or administering at least one therapeutic 224 to the body 14 of the individual 12 (step 614). This administering step 614 can be accomplished by the wearable member 18 directly using the applicator 226. This administering step 614 can also be performed through the wearable member 18 communicating an administering instruction to a separate wearable device or separate exogenous device, as described herein. It is contemplated that this recommended action can be taken remotely by being initiated by a healthcare provider to activate the applicator 226 of the wearable member 18 or remotely activating the wearable member to administer the recommended action via the wearable member 18 directly or through a separate wearable device or separate exogenous device (step 616).

According to various aspects of the device, the healthcare interface 210 can be used to provide remote healthcare services by monitoring the biometric indicators 16 of the body 14 of the individual 12. These monitored biometric indicators 16 provide information regarding whether certain remedial actions 222 should be taken or whether certain individuals 12 should be contacted. In addition, the monitored biometric indicators 16 provide information about whether the individual 12 is in a personal baseline state of health at a particular time. Moreover, use of a healthcare interface 210 can provide a mechanism for treating certain conditions that may be commonly seen within individuals 12 having a diminished capacity to communicate their healthcare status. As discussed herein, such individuals 12 can include infants, some minors, and other individuals 12 with diminished communicative capacity. It should be readily understood that the healthcare interface 210 and the various aspects of the wearable member 18, as disclosed herein, can be used for any individual to assist in the diagnosis, treatment, and/or management of any health condition or illness and for communicating with a healthcare provider and a healthcare team.

Using the healthcare interface 210, the wearable member 18 can be utilized as a communication device between the individual 12, the caregiver as a remote system of healthcare. In addition, aspects of the healthcare interface 210 can incorporate a communications link with a healthcare provider for providing remote virtual healthcare visits. These remote healthcare visits can provide various levels of timely treatments at initial stages of certain conditions during a period of change in health. As discussed herein, treatments at the initial stages of these conditions can greatly reduce the progression of the illness or condition which can, in turn, reduce the severity, duration, and/or complications from the condition. These treatments can ultimately reduce the required interventions and treatments needed for minimizing the effects of these conditions. Accordingly, use of the wearable member 18 and the healthcare interface 210 can decrease the number of healthcare interventions, the length of healthcare interventions, and in turn, the cost of healthcare interventions.

It is to be understood that variations and modifications can be made on the aforementioned structure without departing from the concepts of the present invention, and further it is to be understood that such concepts are intended to be covered by the following claims unless these claims by their language expressly state otherwise.

What is claimed is:

1. A portable biometric healthcare interface comprising:
   a wearable member having a plurality of sensors incorporated therein, each sensor of the plurality of sensors adapted to monitor a corresponding biometric indicator; and
   a communications hub in communication with the plurality of sensors;
   wherein the wearable member and the communications hub cooperatively include a set of biometric parameters, wherein each biometric parameter of the set of biometric parameters includes a corresponding preferred range; and
   when at least one of the sensors indicates that the corresponding biometric indicator is outside of the corresponding preferred range, the communications hub provides a status indicia corresponding to a proposed recommendation, wherein one of the wearable member and the communications hub delivers the proposed recommendation in a form of a proposed remedial action, wherein the proposed remedial action includes the wearable member facilitating at least one of performance of a diagnostic action and administration of a therapeutic, wherein the proposed remedial action to be taken is remotely initiated by a healthcare provider to activate an interface portion of the wearable member, and wherein the interface portion of the wearable member includes an applicator.

2. The portable biometric healthcare interface of claim 1, wherein the communications hub is incorporated within the wearable member.

3. The portable biometric healthcare interface of claim 1, wherein the biometric indicator includes at least two of heart rate, temperature, respiratory rate, oxygen saturation, global positioning system data and inspiration and expiration ratio.

4. The portable biometric healthcare interface of claim 1, further comprising:

a processor that monitors the biometric parameters in relation to the corresponding preferred ranges.

5. The portable biometric healthcare interface of claim 1, wherein the proposed remedial action is remotely initiated by the healthcare provider, via the communications hub.

6. The portable biometric healthcare interface of claim 4, wherein the proposed remedial action is provided based upon the processor evaluating the biometric parameters in relation to the corresponding preferred ranges.

7. The portable biometric healthcare interface of claim 1, wherein the proposed recommendation is configured to be provided to at least one specifically identified individual.

8. The portable biometric healthcare interface of claim 1, wherein the corresponding preferred ranges of the biometric parameters are defined during an evaluation period where the wearable member is attached to a monitored individual.

9. A method of providing remote healthcare based upon monitored biometric function of an individual, the method comprising steps of:
   placing a wearable member onto a portion of an individual's body, wherein a plurality of sensors within the wearable member are positioned to monitor corresponding biometric indicators;
   monitoring the corresponding biometric indicators;
   comparing each biometric indicator with a corresponding biometric parameter, wherein each corresponding biometric parameter includes a corresponding preferred range;
   providing a status indicia when at least one of the biometric indicators falls outside the preferred range of the corresponding biometric indicators; and
   providing a proposed recommendation regarding action to be taken with respect to the individual's body, wherein the action to be taken includes the wearable member facilitating at least one of performance of a diagnostic action and administration of a therapeutic, wherein the action to be taken is remotely initiated by a healthcare provider to activate an interface portion of the wearable member, and wherein the interface portion of the wearable member includes an applicator.

10. The method of claim 9, wherein the corresponding biometric parameters and the corresponding preferred ranges are stored within the wearable member.

11. The method of claim 9, further comprising a step of:
    placing the plurality of sensors in wireless communication with a communications hub, wherein the communications hub includes a set of biometric parameters that includes each corresponding biometric parameter.

12. The method of claim 9, wherein the corresponding biometric indicators include at least two of heart rate, temperature, respiratory rate, oxygen saturation, global positioning data and inspiration and expiration ratio.

13. A method of monitoring a biometric function of an individual, the method comprising steps of:
    placing a wearable member onto a portion of an individual's body, wherein a plurality of sensors within the wearable member are positioned to monitor corresponding biometric indicators;
    placing the plurality of sensors in communication with a communications hub, wherein the communications hub includes a set of biometric parameters, wherein each biometric parameter of the set of biometric parameters includes a preferred range;
    monitoring the corresponding biometric indicators using the plurality of sensors;
    comparing each biometric indicator with the corresponding preferred range of the corresponding biometric indicators;
    providing a status indicia when at least one of the biometric indicators falls outside the preferred range of the corresponding biometric indicators;
    delivering the status indicia to a healthcare provider, wherein the wearable member is configured to remotely receive a recommended action to be taken from the healthcare provider, wherein the recommended action to be taken is remotely initiated by the healthcare provider to activate an applicator of the wearable member.

14. The method of claim 13, wherein the recommended action to be taken includes the wearable member facilitating at least one of performance of a diagnostic action and administration of a therapeutic.

15. The portable biometric healthcare interface of claim 1, wherein the applicator is configured to apply at least one of a topical therapeutic, a transdermal therapeutic, an optic therapeutic, and an otic therapeutic.

16. The portable biometric healthcare interface of claim 1, wherein the applicator is one of integral with the wearable member and an exogenous device that is coupled with the wearable member.

17. The method of claim 9, wherein the applicator is configured to apply at least one of a topical therapeutic, a transdermal therapeutic, an optic therapeutic, and an otic therapeutic.

18. The method of claim 9, wherein the diagnostic action includes at least one of an ancillary diagnostic test, a confirmatory diagnostic test, and monitoring diagnostic after the administration of the therapeutic.

19. The method of claim 13, wherein the applicator is configured to apply at least one of a topical therapeutic, a transdermal therapeutic, an optic therapeutic, and an otic therapeutic.

20. The method of claim 14, wherein the diagnostic action includes at least one of an ancillary diagnostic test, a confirmatory diagnostic test, and monitoring diagnostic after the administration of the therapeutic.

* * * * *